United States Patent [19]
McKittrick et al.

[11] Patent Number: 5,824,683
[45] Date of Patent: Oct. 20, 1998

[54] 2'-[[4'-HALO-[1,1'-BIPHENYL]-4-YL]
METHYL]-5'-METHYL-SPIRO
[CYCLOPENTANE-1,7' (8'H)-[3H] IMIDAZO
[2,1-B]PURIN]-4' (5'H)-ONES

[75] Inventors: Brian A. McKittrick, Bloomfield, N.J.;
Deen Tulshian, Lebanon, N.J.

[73] Assignee: Schering Corporation, Kenilworth, N.J.

[21] Appl. No.: 756,508

[22] Filed: Nov. 26, 1996

Related U.S. Application Data

[60] Provisional application No. 60/007,622 Nov. 28, 1995.
[51] Int. Cl.[6] ..................... A61K 31/505; C07D 487/14; C07D 473/18; C07D 473/40
[52] U.S. Cl. .................... 514/257; 544/230; 544/264; 544/276; 544/311; 562/492; 568/425
[58] Field of Search ............................... 544/230; 514/257

[56] References Cited

U.S. PATENT DOCUMENTS

| | | | |
|---|---|---|---|
| 5,270,316 | 12/1993 | Suzuki et al. | 514/267 |
| 5,352,788 | 10/1994 | Bernhart et al. | 544/6 |
| 5,393,755 | 2/1995 | Neustadt et al. | 514/233.2 |

FOREIGN PATENT DOCUMENTS

| | | |
|---|---|---|
| WO91/19717 | 12/1991 | WIPO . |
| WO94/19351 | 9/1994 | WIPO . |

OTHER PUBLICATIONS

Baum et al, *J. Cardiovasc. Pharmacol.*, 5 (1983), pp. 655–667.

*Primary Examiner*—Mark L. Berch
*Attorney, Agent, or Firm*—Anita W. Magatti

[57] ABSTRACT

Antihypertensive and bronchodilating phosphoclusterose inhibitory compounds of the formula

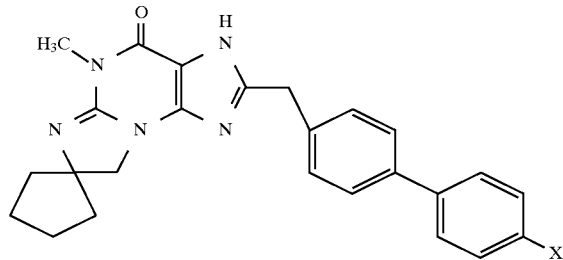

or a pharmaceutically acceptable salt thereof wherein X is fluoro, chloro or bromo.

6 Claims, No Drawings

2'-[[4'-HALO-[1,1'-BIPHENYL]-4-YL]METHYL]-5'-METHYL-SPIRO[CYCLOPENTANE-1,7' (8'H)-[3H] IMIDAZO[2,1-B]PURIN]-4' (5'H)-ONES

BACKGROUND

The present invention relates to 2'-[[4'-halo-[1,1'-biphenyl]-4-yl]methyl]-5'-methyl-spiro[cyclopentane-1,7' (8'H)-[3H]imidazo[2,1-b]purin]-4'(5'H)-ones, their use in treating cardiovascular and pulmonary disorders, and pharmaceutical compositions comprising them. Phosphodiesterase inhibitory compounds of this invention were generically but not specifically disclosed in PCT publication WO91/19717, published Dec. 26, 1991, and related compounds were generically and specifically disclosed in WO94/19351, published Sep. 1, 1994. We have found that the compounds of the present invention show unexpectedly superior plasma levels compared to the compounds of the prior publications when administered intravenously, subcutaneously or orally.

SUMMARY OF THE INVENTION

The present invention is directed to 2'-[[4'-halo-[1,1'-biphenyl]-4-yl]methyl]-5'-methyl-spiro[cyclopentane-1,7' (8'H)-[3H]imidazo-[2,1-b]purin]-4'(5'H)-ones of the formula I:

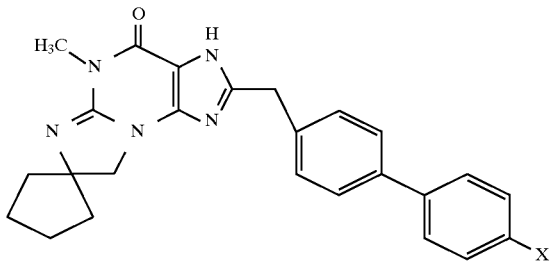

or a pharmaceutically acceptable salt thereof, wherein:
X is fluoro, chloro or bromo.

The compounds of formula I are useful as antihypertensive, bronchodilating and blood platelet inhibiting agents. Compounds of the invention are useful in inhibiting phosphodiesterase enzymes; the inhibition of vascular phosphodiesterase is associated with vasodilation and vasorelaxation, and therefore is expected to induce antihypertensive and antianginal activity. Compounds of formula I can also serve as smooth muscle relaxants and are therefore useful in the treatment of bronchoconstriction. Such compounds also can inhibit smooth muscle proliferation, vascular growth and platelet function and are useful in treating conditions such as restenosis post angioplasty, atherosclerosis and conditions which benefit from inhibiting platelet function. Through one or more of the above physiological mechanisms, compounds of formula I are also useful in treating ischemia and peripheral vascular diseases.

Compared to previously known phosphodiesterase inhibitors of similar structure, the compounds of the present invention are not as readily metabolized. They demonstrate good selectivity of inhibition of Type I and Type V phosphodiesterase isozymes while maintaining high blood levels and demonstrating antiplatelet and vasodilator activity.

The present invention is also directed toward a pharmaceutical composition containing a compound of formula I in an amount effective to inhibit phosphodiesterase enzymes, smooth muscle proliferation, vascular growth or platelet function, or to relax smooth muscle. The present invention is also directed toward a pharmaceutical composition containing an anti-hypertensive, an anti-anginal, a bronchodilating or a platelet inhibiting effective amount of a compound of formula I.

The present invention is also directed toward a method for treating hypertension, angina, bronchoconstriction, restenosis post angioplasty, atherosclerosis, ischemia, peripheral vascular diseases, or diseases benefitting from platelet inhibition in a mammal comprising administering to a mammal in need of such treatment an amount of a compound of formula I effective to treat any of the above diseases. The present invention is also directed toward a method for maintaining guanosine 3',5'-cyclic monophosphate (cGMP) levels in a mammal by administering an amount of a compound of formula I effective to maintain or increase cGMP levels.

DETAILED DESCRIPTION OF THE INVENTION

Compounds of the invention have a basic nitrogen containing moiety, and can form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner.

The compounds of the present invention can be prepared by several routes, such as those described in WO91/19717 and WO94/19351. The following examples show typical procedures, but those skilled in the art will recognize that the preparation of these compounds is not limited to these procedures. In the examples below, Me refers to methyl, Bn refers to benzyl, Ph refers to phenyl and SEM refers to trimethylsilylethoxymethyl.

EXAMPLE 1

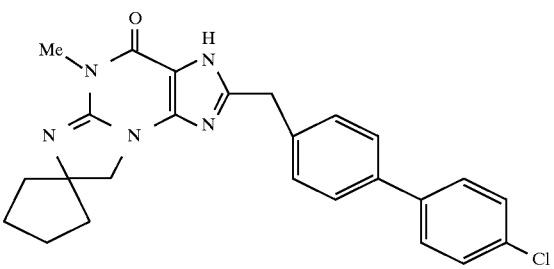

Step 1:

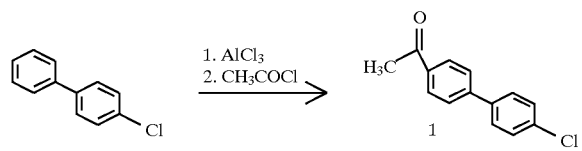

To a stirred ice-cold solution of 4-chlorobiphenyl (115 g, 0.61 mol) in $CH_2Cl_2$ (1200 ml) add $AlCl_3$ (97.5 g, 0.73 mol) in portions over 0.5 h. Add acetyl chloride (48 ml, 0.68 mol) dropwise over 0.75 h and stir the resultant red reaction mixture at 0°–5° C. After 3.5 h, allow the reaction mixture to warm to 10° C., then pour onto a slurry of ice/1M HCl (1000 ml) with vigorous stirring. Allow the mixture to stand overnight, then wash the organic layer with sat'd NaCl, dry (MgSO$_4$), filter and evaporate to give a pale yellow solid. Triturate the solid with ether and collect to give the ketone 1 (122 g, 87%). $^1$H NMR CDCl$_3$ δ 8.01 m, 2H; 7.62 m, 2H; 7.53 m, 2H; 7.41 m, 2H; 2.62 s, 3H.

Step 2:

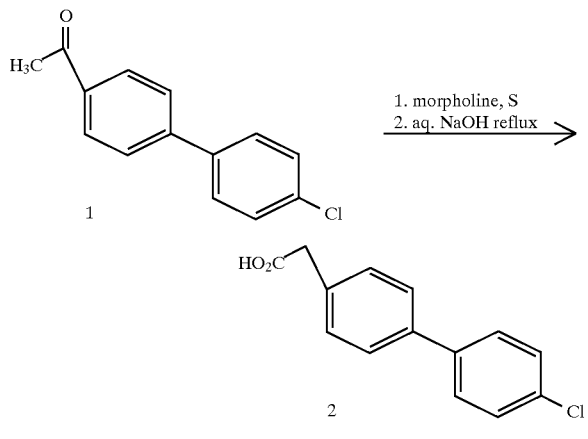

Heat a mixture of the ketone 1 (60 g, 0.26 mol), sulfur (12.5 g, 0.39 mol) and morpholine (38 ml, 0.43 mol) at reflux. After 28 h, add the resultant brown solid to a solution of NaOH (240 g) in water (1200 ml). Reflux the mixture for 24 h, cool, collect the precipitate, wash with water and air-dry. Suspend the solid in hot water (2000 ml) and acidify to pH 2 with approximately 200 ml 1M HCl. Allow the mixture to cool, collect the solid, wash with water and air-dry. Take up the solid into EtOAc (1000 ml), wash with sat'd NaCl, dry (MgSO$_4$), filter and evaporate to dryness to give the acid 2 (54.9 g, 86%) as a brown solid. $^1$H NMR CDCl$_3$ δ 7.52 m, 4H; 7.40 m, 4H; 3.72 s, 2H.

Step 3:

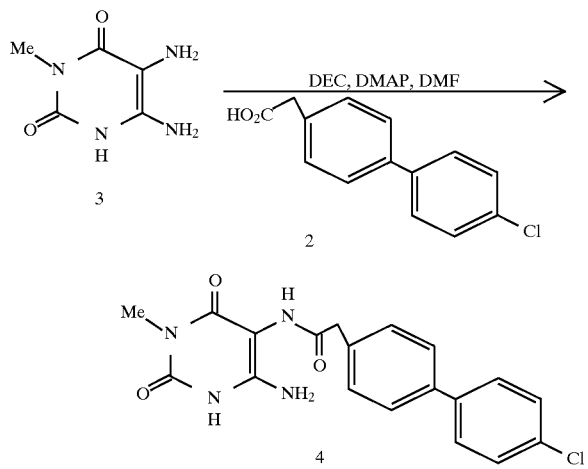

To a stirred solution of the diaminouracil 3 (33.3 g, 0.21 mol), acid 2 (58.0 g, 0.24 mol) and 4-dimethylaminopyridine (2.6 g, 0.021 mol) in DMF (1000 ml), add 1-(3-dimethylaminopropyl)-3-ethylcarbodiimide methiodide (76 g, 0.26 mol). Stir overnight at room temperature, then pour the reaction mixture onto an ice water slurry (3000 ml). Collect the solid, wash with water and ethanol, and dry in vacuo to give the amide 4 (69.9 g, 87%) which is used without further purification. $^1$H NMR DMSO-d6 δ 10.51 s, 1H; 8.64 s, 1H; 7.70-7.40 m, 8H; 6.01 s, 2H; 3.65 s, 2H; 3.02 s, 3H.

Step 4:

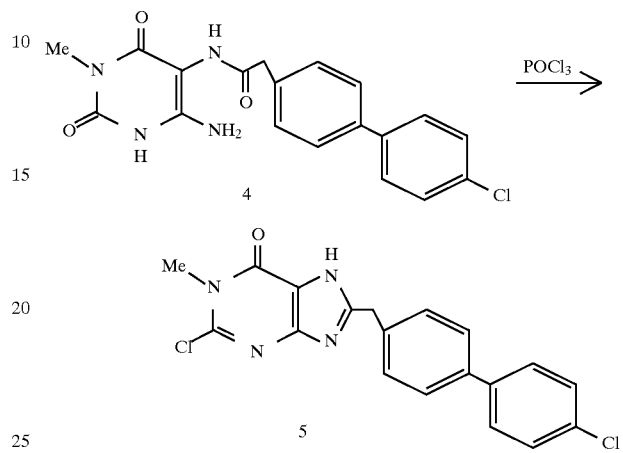

Heat a stirred suspension of the amide 4 (45.0 g, 0.117 mole) in POCl$_3$ (1500 ml) at 90°–95° C. for 43 h, then at 100° C. for 16 h, then at 110° C. for 8 h. Remove the POCl$_3$ by distillation at reduced pressure and cool the resultant oil in an ice bath. Neutralize residual POCl$_3$ by careful addition of saturated NaHCO$_3$ and collect, the resultant solid by filtration, wash several times with water, air-dry, then dry in vacuo at 50° C. Triturate the solid (53 g) with 9:1 CH$_2$Cl$_2$/CH$_3$OH (1000 ml), collect and then triturate further with 1:1 CH$_3$OH/CH$_2$Cl$_2$ with gentle heating. Concentrate the filtrate in vacuo to obtain the chloropurine 5 (25.6 g) as a brown solid. Concentrate the filtrate from the 9:1 CH$_2$Cl$_2$/CH$_3$OH trituration in vacuo and take up in the minimum volume of approximately 4:1 CH$_2$Cl$_2$/CH$_3$OH. Add hexanes to the resultant solution until solids begin to separate. Collect the brown solid and wash with CH$_2$Cl$_2$ to obtain additional chloropurine 5 (6.0 g). Use the chloropurine (combined yield after drying in vacuo 31.0 g, 69%) in the next step without further purification. $^1$H NMR CDCl$_3$ δ 7.53-7.46 m, 4H; 7.41-7.37 m, 4H; 4.31 s, 2H; 3.75 s, 3H.

Step 5:

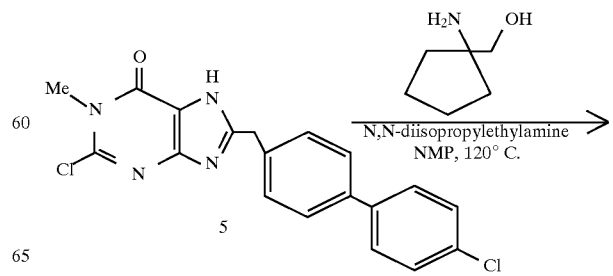

-continued

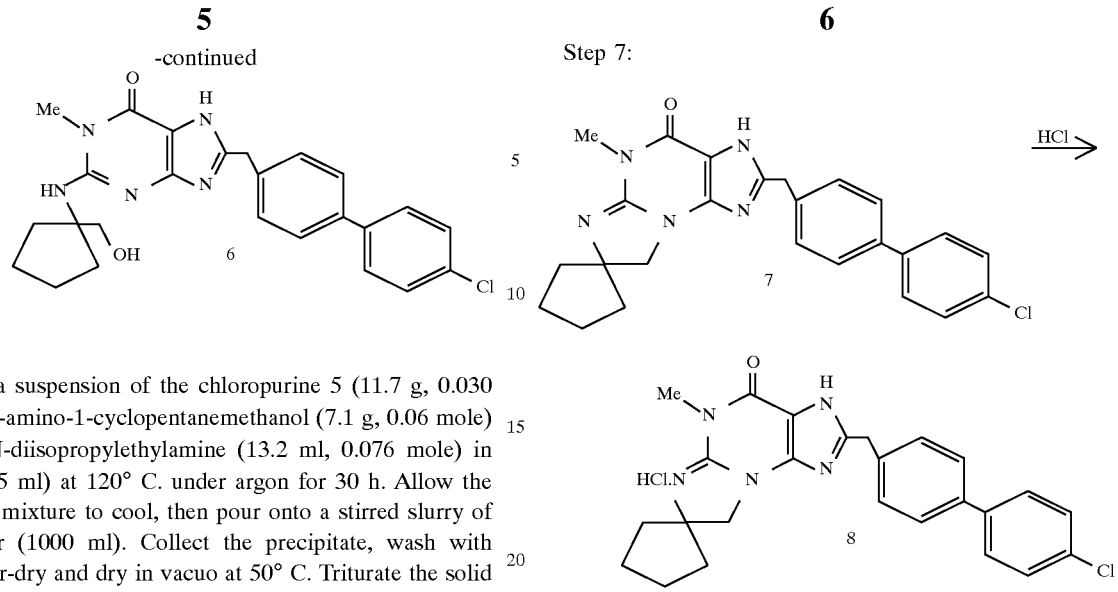

Heat a suspension of the chloropurine 5 (11.7 g, 0.030 mole), 1-amino-1-cyclopentanemethanol (7.1 g, 0.06 mole) and N,N-diisopropylethylamine (13.2 ml, 0.076 mole) in NMP (25 ml) at 120° C. under argon for 30 h. Allow the reaction mixture to cool, then pour onto a stirred slurry of ice/water (1000 ml). Collect the precipitate, wash with water, air-dry and dry in vacuo at 50° C. Triturate the solid (13.3 g) with warm 1:1 $CH_2Cl_2/CH_3OH$, then filter. Adsorb the filtrate onto silica gel (75 g) and flash chromatograph (24:1 $CH_2Cl_2/CH_3OH$, then 19:1 $CH_2Cl_2/CH_3OH$ when the product begins to elute) to obtain the alcohol 6 (7.5 g, 53%) as an off-white solid. Calcd for $C_{25}H_{26}N_5O_2Cl.0.75 H_2O$: C, 62.11; H, 5.73; N, 14.49. Found: C, 62.38; H, 5.59; N, 14.30%. MS (FAB) m/z 466.1, 464.1 $(M+H)^+$.

Step 6:

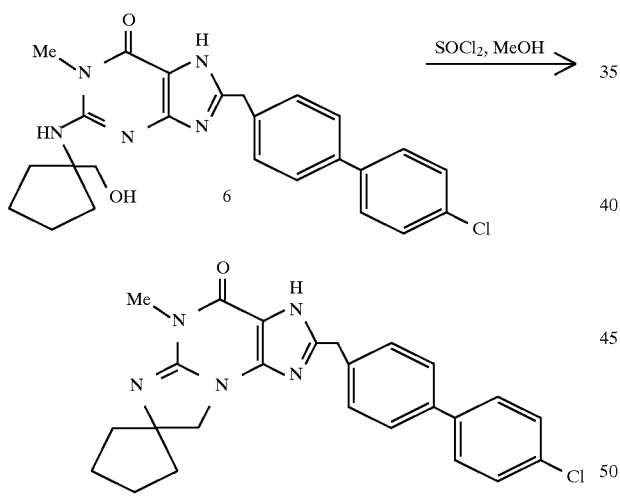

To a stirred suspension of the alcohol 6 (12.1 g, 0.026 mol) in $CH_2Cl_2$ (750 ml), add $SOCl_2$ (5.7 ml, 0.078 mol) rapidly dropwise. Stir the reaction mixture vigorously for 3 h, then evaporate in vacuo. Dissolve the residue in $CH_3OH$ (100 ml), filter and pour the filtrate into a rapidly stirred solution of 10% $NaHCO_3$. Collect the precipitate, wash with water (1000 ml) and $CH_3OH$ (150 ml), then dry. Recrystallize from $CH_3OH/CH_2Cl_2$ to obtain the product 7 as an off-white powder (10.30 g, 88%). Calcd for $C_{25}H_{24}N_5OCl$: C, 67.33; H, 5.42; N, 15.70; Cl, 7.95 Found: C, 67.41; H, 5.66; N, 15.41; Cl, 8.24%. MS (FAB) m/z 448.3, 446.3 $(M+H)^+$.

Step 7:

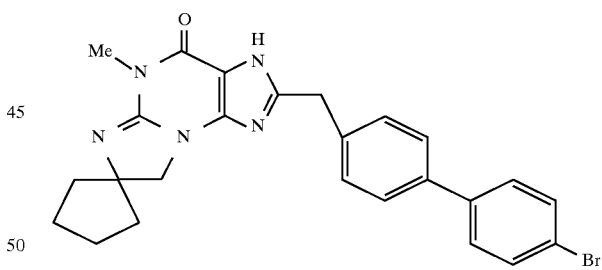

To a suspension of the tetracyclic guanine 7 (10.30 g, 0.023 mol) in EtOH (125 ml) warmed on a steam bath, add conc. HCl (1.9 ml, 0.023 mol). Filter the resultant cloudy mixture and wash the filter pad with warm EtOH (75 ml). To the combined filtrate and washings, add hot water (100 ml) and allow the solution to stand. Collect the crystalline mass, wash with 1:1 $EtOH/H_2O$, air-dry and dry in vacuo at 50° C. to obtain the hydrochloride 8 (7.0 g, 63%). A second crop of product 8 (3.0 g, 27%) is obtained from the mother liquor. Combine the two crops and dry in vacuo at 50° C. over $P_2O_5$. Calcd for $C_{25}H_{25}N_5OCl_2.1.75H_2O$: C, 58.43; H, 5.59; N, 13.63; Cl, 13.80. Found: C, 58.45; H, 5.24; N, 13.45; Cl, 13.70%. $^1H$ NMR $CD_3OD$ δ 7.58-7.56 m, 4H; 7.43-7.37 m, 4H; 4.38 s, 2H; 4.19 s, 2H; 3.46 s, 3H; 2.10-1.79 m, 8H.

EXAMPLE 2

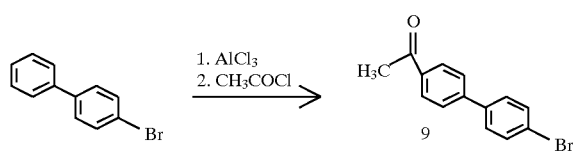

Step 1:

Use the procedure of Example 1, Step 1, with bromobiphenyl (51.36 g, 0.22 mol) to obtain ketone 9 (50.94 g, 84%) as a light yellow solid. $^1H$ NMR $CDCl_3$ δ 8.03 dd (J=6.6 and 2.2 Hz), 2H; 7.65 dd (J=6.6 and 2.2 Hz), 2H; 7.55 dd (J=6.6 and 2.2 Hz), 2H; 7.49 dd (J=6.6 and 2.2 Hz), 2H; 2.64 s, 3H.

Step 2:
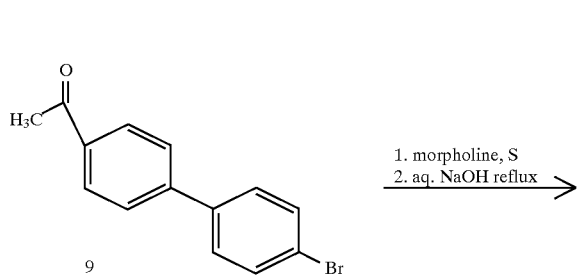
Use the procedure of Example 1, Step 2, heating with sulfur and morpholine for 4 h, to convert ketone 9 (50.93 g, 0.19 mol) to acid 10 (51.3 g, 95%), a white solid. $^1$H NMR DMSO-d6 δ 7.65–7.59, m, 6H; 7.35 d (J=8.2 Hz), 2H; 3.60 s, 2H.
Step 3:
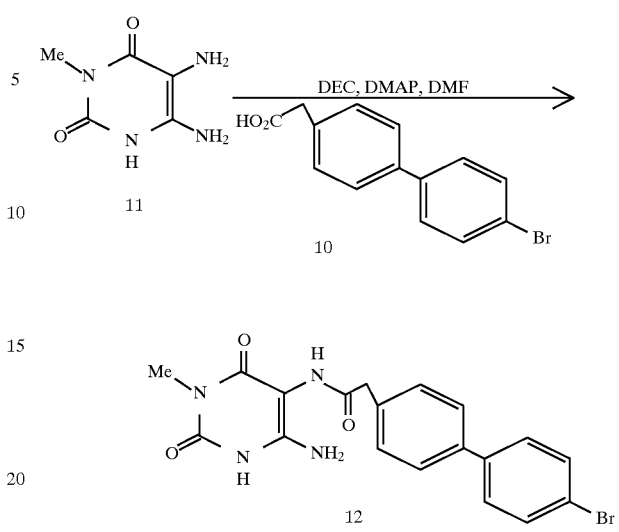
Treat acid 10 (51.3 g, 0.18 mol) using the procedure of Example 1, Step 3, to obtain amide 12 (61.2 g, 82%) as a yellow solid. $^1$H NMR DMSO-d6 δ 10.52 s, 1H; 8.66 s, 1H; 7.66–7.59 m, 6H; 7.43 d (J=8.2 Hz), 2H; 6.01 s, 2H; 3.61 s, 2H; 3.04 s, 3H.
Step 4:
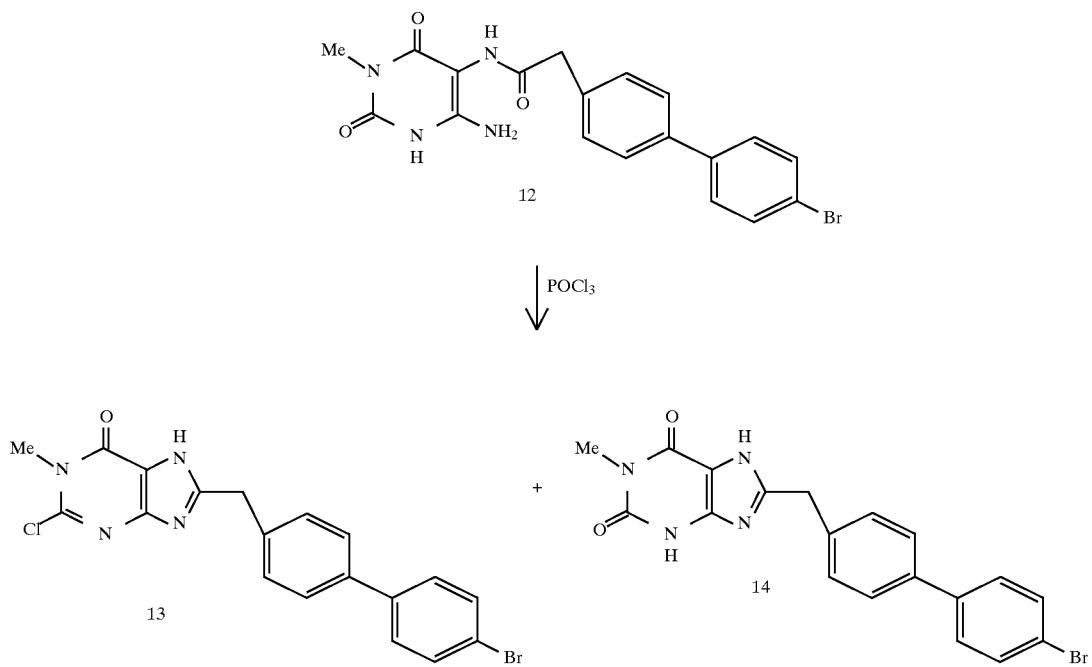

Heat a stirred suspension of the amide 12 (40.0 g, 0.093 mole) in POCl₃ (2100 ml) at 90°–100° C. for 6 days. Remove the POCl₃ by rotovaporation at reduced pressure (<45° C.) and dissolve the resultant oil in a minimal amount of CH₂Cl₂ (~400 ml). Neutralize the residual POCl₃ by carefully pouring the CH₂Cl₂ solution into cold saturated NaHCO₃ (2200 ml) over a period of 1 h. Stir the mixture overnight at room temperature, collect the resultant solid by filtration, wash several times with water, air-dry and dry in vacuo at 60° C. The solid (28.47 g, 71%) is a 26:1 mixture of chloropurine 13 and xanthine 14, respectively (¹H NMR analysis). ¹H NMR CDCl₃ δ 7.64-7.58 m, 6H; 7.38 d (J=8.2 Hz), 2H; 4.13 s, 2H; 3.61 s, 3H.

Step 5:

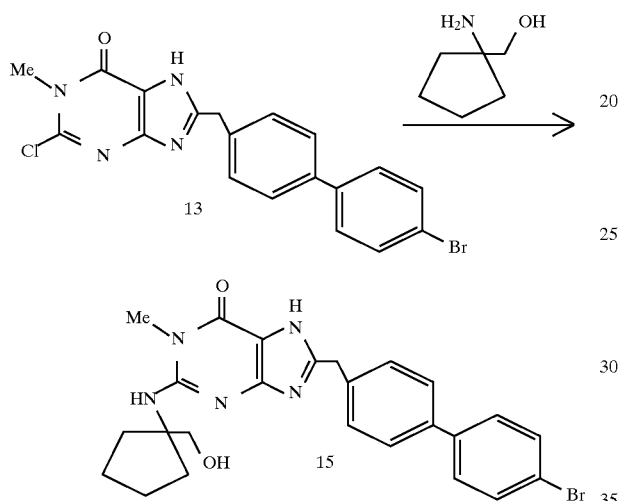

Heat a suspension of the chloropurine 13 (28.57 g, 0.066 mole), 1-amino-1-cyclopentanemethanol (19.77 g, 0.17 mole) and N,N-diisopropylethylamine (30 ml, 0.17 mole) in NMP (96 ml) at 120° C. under argon for 18 h. Cool the reaction mixture, then pour onto a stirred slurry of ice/brine (1000 ml). Collect the precipitate, wash with water, air-dry and dry in vacuo at 50° C. Triturate the solid (42.36 g) with CH₂Cl₂-CH₃OH (4:1), and then filter to give 17.48 g of a solid consisting of alcohol 15 and xanthine 14. Adsorb the filtrate onto silica gel and subject to flash chromatography [gradient CH₂Cl₂/CH₃OH=32:1 to 19:1 (product begins eluting) to 11.5:1] to obtain alcohol 15 (7.4 g, 22%) as an off-white solid and impure 15 (5.79 g) containing xanthine 14. ¹H NMR CDCl₃ δ 7.64-7.58 m, 6H; 7.37 m, 2H; 5.76-5.63 m, 1H; 5.09, 4.89 t,t (J=5.8 Hz), 1H; 4.02, 3.97 s, s, 2H; 3.64 d (J=5.8 Hz), 2H; 3.36 s, 3H; 2.05 m, 2H; 1.72 m, 4H; 1.53 m, 2H.

Step 6:

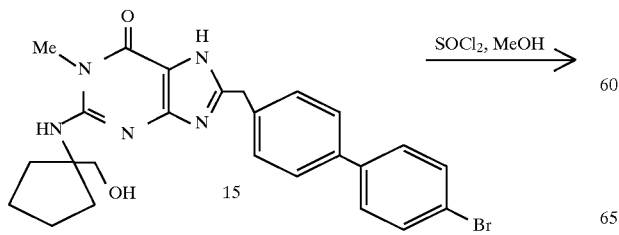

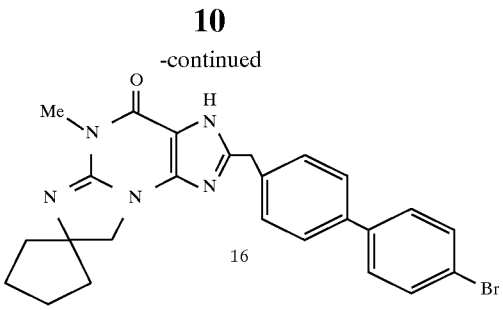

Treat alcohol 15 (10.1 g, 0.020 mol) according to the procedure of Example 1, Step 6, to obtain tetracyclic guanine 16 (9.6 g, 95%) as a white solid. ¹H NMR DMSO-d6 δ 7.65-7.58, m, 6H; 7.37, d (J=8.2 Hz), 2H; 4.02 s, 2H; 4.80 s, 2H; 3.18 s, 3H; 1.75-1.62 m, 8H.

Step 7:

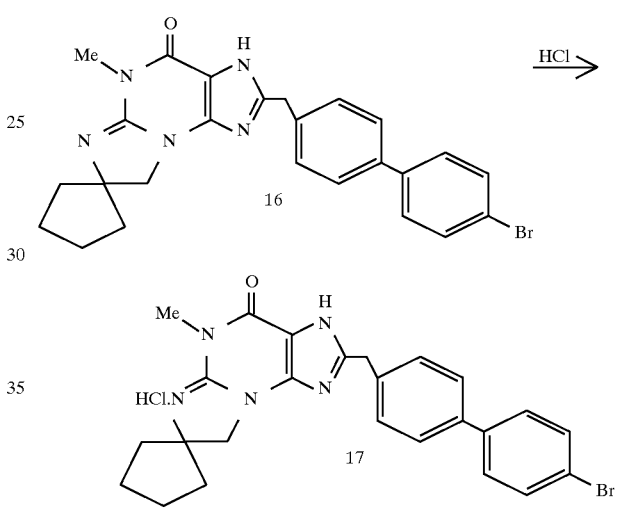

Using a procedure similar to Example 1, Step 7, except recrystallizing twice from CH₃OH and then twice from ethanol-water, treat the amine 16 (11.7 g, 0.024 mol) to obtain the hydrochloride 17 (10.22 g, 81%) as a white solid. Calcd for C₂₅H₂₅N₅OBrCl.3H₂O: C, 51.69; H, 5.39; N, 12.06; Br, 13.75; Cl, 6.10. Found: C, 51.58; H, 5.63; N, 11.84; Br, 13.55; Cl, 5.77%. MS (FAB) m/z 490.1, 491.1 (M+H). ¹H NMR DMSO-d6+D₂O δ 7.63-7.56, m, 6H; 7.37, d (J=8.2 Hz), 2H; 4.28 s, 2H; 4.12 s, 2H; 3.31 s, 3H; 1.98-1.87 m, 4H; 1.79-1.61 m, 4H.

EXAMPLE 3

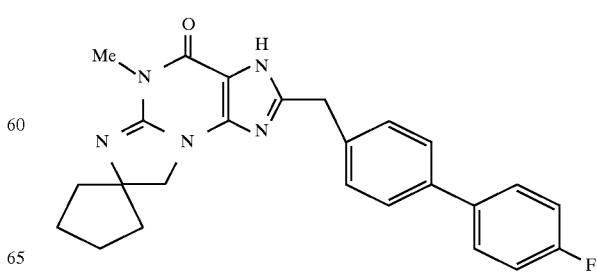

Step 1:

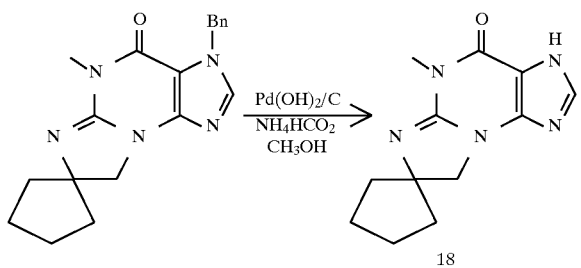

To a suspension of Pd(OH)₂ (5 g) in CH₃OH, add HNH₄CO₂ (14 g, 223 mmol) followed by a solution of 5'-methyl-3'-(phenylmethyl)-spiro[cyclopentane-1,7'(8'H)-[3'H]-imidazo[2,1-b]purin]-4'(5'H)-one (15 g, 44.7 mmol) in CH₃OH (total volume 1000 ml) at room temperature. Heat the mixture at reflux for 6 h, filter and concentrate the filtrate to obtain a white solid. Stir the catalyst in hot 10% CH₃OH/CH₂Cl₂, filter and concentrate. Combine the concentrated filtrates, dissolve in 10% CH₃OH/CH₂Cl₂ (400 ml) and wash with aqueous NaHCO₃. Extract the aqueous solution with 10% CH₃OH/CH₂Cl₂ (200 ml×2), dry the combined extracts over MgSO₄, filter and concentrate to obtain compound 18 as a white solid (9.7 g, 88.5%). $^1$H NMR CDCl₃ δ 7.62, s, 1H; 3.95, s, 2H; 3.40, s, 3H; 1.8–2.0, m, br, 4H; 1.6–1.8, m, br, 4H.

Step 2:

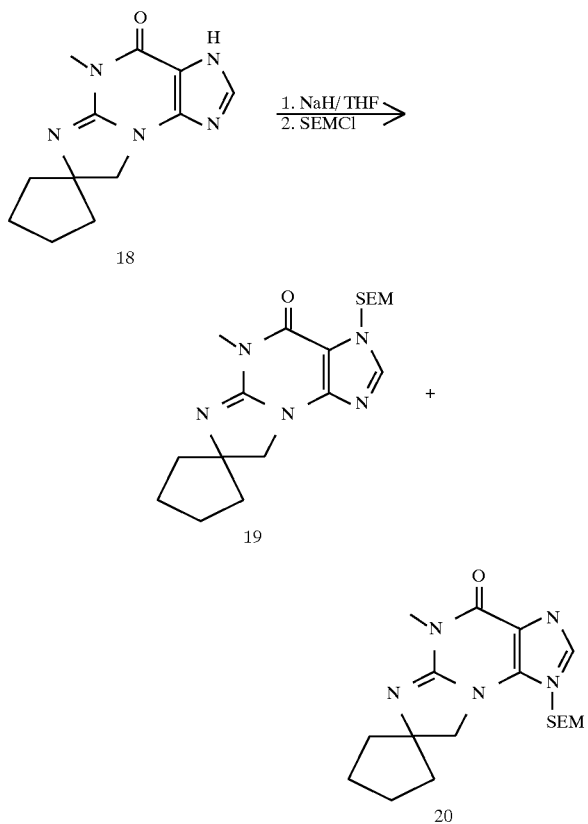

Add NaH (3.16 g, 60%, 79 mmol) to a mixture of 18 (9.7 g, 39.5 mmol) in THF (400 ml) at room temperature. Stir the mixture at room temperature for 1.5 h, add trimethylsilylethoxymethyl chloride (9.88 g, 59.25 mmol) and stir at room temperature for 1.5 h. Quench the resulting yellow mixture with ice, extract with EtOAc (200 ml×2), combine the EtOAc extracts and wash with brine, dry over MgSO₄, filter and concentrate. Purify the crude product by flash chromatography on SiO₂ (1% to 10% CH₃OH/CH₂Cl₂) to obtain compounds 19 (11.4 g), 20 (2.37 g) and a mixture of 19 and 20 (1.1 g) (98%). $^1$H NMR of 19 CDCl₃ δ 7.61, s, 1H; 5.65, s, 2H; 3.91, s, 2H; 3.62, t, 2H; 3.38, s, 3H; 1.8–2.0, m, 4H; 1.6–1.8, m, 4H; 0.95, t, 3H; 0.00, s, 9H. $^1$H NMR of 20 CDCl₃ d 7.26, s, 1H; 5.32, s, 2H; 4.00, s, 2H; 3.53, t. 2H; 3.40, s, 3H; 1.8–2.0, m, 4H; 1.6–1.8, br, 4H; 0.92, t, 2H; 0.00, s, 9H.

Step 3:

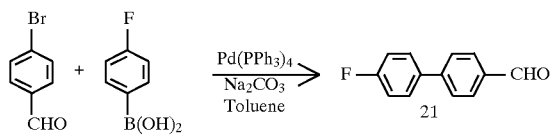

To a mixture of Pd(PPh₃)₄ (1.5 g, 1.3 mmol) in toluene (52 ml), add p-bromobenzaldehyde (4.8 g, 25.98 mmol), aqueous Na₂CO₃ (26 ml, 2.0M, 52 mmol), and a solution of p-fluorophenylboronic acid (4 g, 28.58 mmol) in EtOH (13 ml) and CH₃OH (2 ml). Heat the mixture at reflux for 6 h, cool to room temperature, pour into aqueous NaHCO₃, extract with EtOAc (200 ml×3), dry over MgSO₄, filter and concentrate to obtain a dark, thick oil. Purify the crude product by flash column chromatography on SiO₂ (1:9, 1:7 EtOAc/hexane) to obtain compound 21 (4.88 g, 93.8%). $^1$H NMR CDCl₃ δ 10.06, s, 1H; 7.96, d, 2H; 7.72, d, 2H; 7.62, dd, 2H; 7.18, t, 2H.

Step 4:

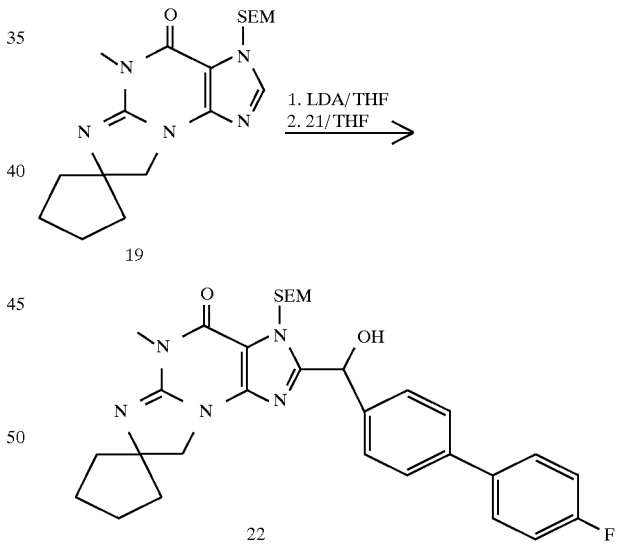

Add n-BuLi (6.65 ml, 2.5M, 16.62 mmol) to a solution of diisopropylamine (1.68 g, 16.62 mmol) in THF (30 ml) at 0° C. Stir at 0° C. for 1 h, cool to −70° C. and add a solution of compound 19 (4.8 g, 12.78 mmol) in THF (60 ml) dropwise. After the addition is complete, stir the mixture at −70° C. for 1 h, then add a pre-cooled solution of 21 (3.85 g, 19.17 mmol) in THF (15 ml). Stir the mixture at −70° C. for 3 h, quench with AcOH(4 ml), warm to 0° C. and treat with aqueous NH₄Cl (30 ml). Extract the mixture with EtOAc (200 ml×3), wash with aqueous NaHCO₃ and brine, dry (MgSO₄) and concentrate. Purify the crude product by flash column chromatography on SiO₂ (0% to 2% CH₃OH/

EtOAc) to obtain compound 22 (5.34 g, 72.6%). $^1$H NMR CDCl$_3$ δ 7.55, m, 4H; 7.54, 2H; 7.15, t, 2H; 6.05, d, br, 1H; 5.56, ABq, 2H; 3.97, s, 2H; 3.60, t, 2H; 3.38, s, 3H; 1.8–2.0, m, 4H; 1.6–1.8, m, 4H; 0.90, m, 2H; 0.00, s, 9H.

Step 5:

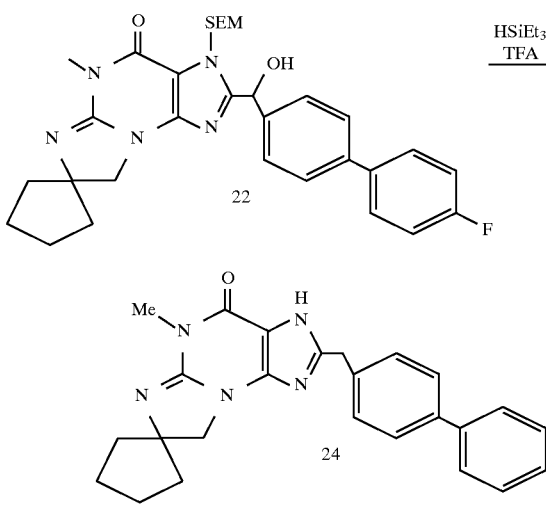

Add EtSiH (5.34 g, 45.4 mmol) to a solution of 22 (5.23 g, 9.08 mmol) in TFA (24 ml) at room temperature. Stir the reaction mixture at room temperature over night, carefully neutralize with aqueous NaHCO$_3$, extract with 10% CH$_3$OH/CH$_2$Cl$_2$, dry over MgSO$_4$, filter and concentrate. Purify the crude product by flash column chromatography on SiO$_2$ (3% to 10% CH$_3$OH/CH$_2$Cl$_2$) to obtain compound 24 (3.35 g). $^1$H NMR CDCl$_3$ δ 7.51, m, 4H; 7.49, d, 2H; 7.11, t, 2H; 4.18, s, 2H; 3.92, s, 2H; 3.39, s, 3H; 1.8–2.0, m, 4H; 1.6–1.8, m, 4H.

Step 6:

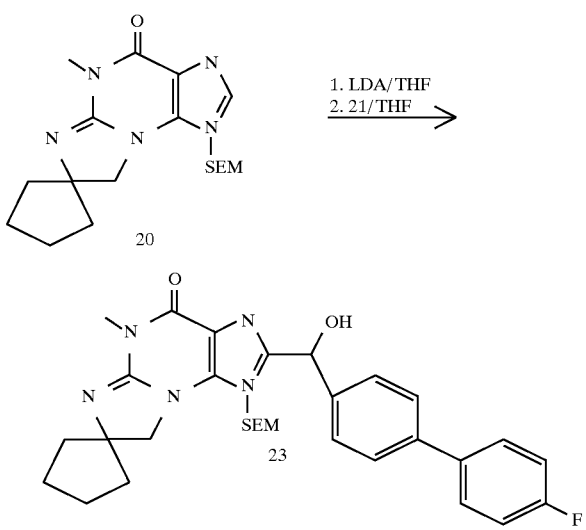

Using compound 20 (8 g, 21.7 mmol) in the procedure of Example 3, Step 4, prepare compound 23 (4.6 g, 37%). $^1$H NMR CDCl$_3$ δ 7.50, m, 6H; 7.10, t, 2H; 6.18, s, 1H; 5.21, s, 2H; 3.99, ABq, 2H; 3.39, s, 3H; 3.10, m, 2H; 1.8–2.0, m, 4H; 1.6–1.8, m, 4H; 0.65, t, 2H; −0.10, s, 9H.

Step 7:

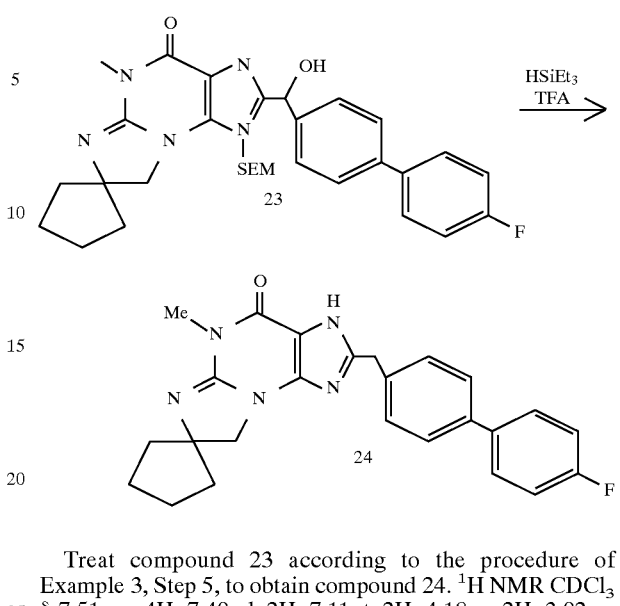

Treat compound 23 according to the procedure of Example 3, Step 5, to obtain compound 24. $^1$H NMR CDCl$_3$ δ 7.51, m, 4H; 7.49, d, 2H; 7.11, t, 2H; 4.18, s, 2H; 3.92, s, 2H; 3.39, s, 3H; 1.8–2.0, m, 4H; 1.6–1.8, m, 4H.

Step 8:

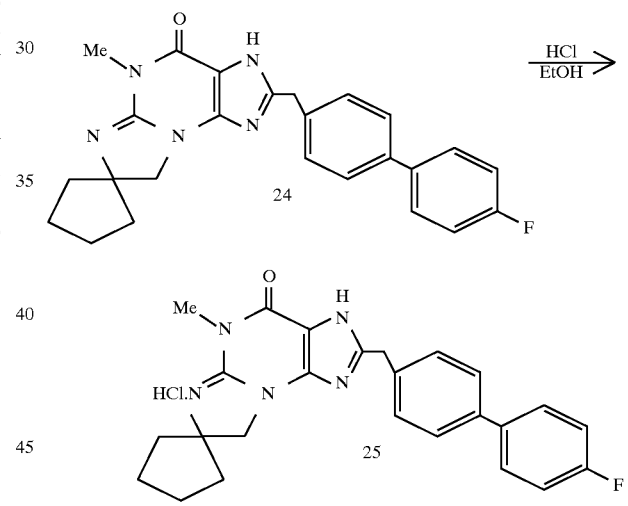

To a hot suspension of 24 (17.5 g, 40.74 mmol) in EtOH, add conc. HCl (5.1 ml, 61.2 mmol) dropwise to give a clear solution. Stir the solution at room temperature for 30 min, evaporate the EtOH to give a white solid and dry the solid in vacuo at 50° C. over P$_2$O$_5$. Calcd for C$_{25}$H$_{24}$N$_5$OF.1.05HCl.0.75H$_2$O: C, 62.39; H, 5.56; N, 14.55; Cl, 7.73, F, 3.95. Found: C, 62.44; H, 5.71; N, 14.38; Cl, 7.80; F, 4.00%. $^1$H NMR DMSO-d6 δ 10.65, d, br, 1H; 7.7, m, 2H; 7.65, d, 2H, 7.40, d, 2H; 7.26, t, 2H; 4.32 s, 2H; 4.19 s, 2H; 3.39 s, 3H; 1.6–2.1 m, 8H.

Pharmaceutical Preparations

The compounds of formula I can be combined with a suitable pharmaceutical carrier to prepare a pharmaceutical composition suitable for parenteral or oral administration. Such pharmaceutical compositions are useful in the treatment of cardiovascular and pulmonary disorders such as mammalian hypertension and bronchoconstriction.

The effective daily antihypertensive dose (ED$_{50}$) of the present compounds will typically be in the range of about 1 to about 100 mg/kg of mammalian body weight, administered in single or divided doses. The exact dosage to be administered can be determined by the attending clinician and is dependent upon where the particular compound lies within the above cited range, as well as upon the age, weight and condition of the individual.

Generally, in treating humans in need of treatment for hypertension or bronchoconstriction, the present compounds can be administered in a dosage range of about 10 to about 500 mg per patient generally given a number of times per day, providing a total daily dosage of from about 10 to about 2000 mg per day.

The compositions of the present invention can be administered orally or parenterally. Typical injectable formulations include solutions and suspensions. Typical oral formulations include tablets, capsules, syrups, suspensions and elixirs. Also contemplated are mechanical delivery systems, e.g. transdermal dosage forms.

The typical acceptable pharmaceutical carriers for use in the formulations described above are exemplified by sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Following are typical examples of oral and parenteral formulations, wherein the term "Active Ingredient" refers to a compound of formula I.

| Capsule | Amount (mg) | |
| --- | --- | --- |
| Active Ingredient | 250.0 | 125.0 |
| Lactose | 173.0 | 86.5 |
| Corn Starch | 75.0 | 37.5 |
| Magnesium Stearate | 2.0 | 1.0 |
| TOTAL | 500.0 | 250.0 |

Blend the active ingredient, lactose and corn starch until uniform; then blend the magnesium stearate into the resulting powder. Encapsulate the mixture into suitably sized two-piece hard gelatin capsules.

| Tablet | Amount (mg) | |
| --- | --- | --- |
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| TOTAL | 500.0 | 250.0 |

Blend the active ingredient with the lactose until uniform. Blend the smaller quantity of corn starch with the water and add the resulting corn starch paste then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

| Injectable Solution | mg/ml |
| --- | --- |
| Active Ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at a temperature of between 60° C.–70° C. and cool the solution to 20° C.–30° C., Charge and dissolve all other excipients and the active ingredient. Bring the solution to final volume, filter it through a sterilizing membrane and fill into sterile containers.

Biological Activity of 2'-[[4'-halo-[1,1'-biphenyl]-4-yl]methyl]-5'-methyl-spiro[cyclopentane-1,7'(8'H) -[3H]imidazo-[2,1-b]purin-4'(5'H)-ones The present compounds are useful in inhibiting phosphodiesterase enzymes, in particular phosphodiesterase isozymes Types I and V. These phosphodiesterase enzymes are known to hydrolyze cGMP in smooth muscle. High levels of cGMP are associated with the relaxation of vascular smooth muscle, with a consequent subsequent reduction in blood pressure. Thus, it is believed that by inhibiting these phosphodiesterase enzymes, cGMP levels in muscle will be either maintained or increased, with a subsequent reduction in blood pressure. In vivo antihypertensive activity is determined orally in spontaneously hypertensive rats (SHR).

Phosphodiesterase inhibition in vitro:

Compounds are evaluated for inhibition of two phosphodiesterase enzymes which hydrolyze cyclic guanosine monophosphate (cGMP). The first enzyme, calcium-calmodulin dependent phosphodiesterase (CaM-PDE), is a partially pure enzyme obtained from bovine aorta homogenates and purified by DEAE-cellulose and calmodulin-affinity chromatography. The enzyme is activated several fold by Ca-calmodulin and is selective for cGMP, although it will also hydrolyze cAMP. The second enzyme, cGMP phosphodiesterase (cGMP-PDE), is a homogeneous enzyme obtained from bovine lung and purified by ion-exchange chromatography, gel filtration, and sucrose gradient centrifugation. cGMP-PDE is highly selective for cGMP. Bovine aorta homogenates and primary cultures of bovine aortic endothelial and vascular smooth muscle cells contain an enzyme with properties very similar to the lung isozyme.

The enzyme assay is performed using a Biomek Automated Pipetting Station. Compounds are dissolved in distilled water or DMSO and diluted with 10% DMSO. Compounds are tested at several concentrations at log intervals, typically 0.1, 1.0, 10, and 100 $\mu$M final concentration.

Assays contain the following components:
1 µM substrate $^3$H-cGMP
50 mM Tris-HCl, pH 7.5, 5 mM $MgCl_2$
0.5 mg/ml snake venom alkaline phosphatase
0.1 µM Calmodulin and 1 mM $CaCl_2$ (for CaM-PDE only)

Assays are initiated by addition of enzyme and stopped by addition of 10 mM isobutylmethylxanthine, a general phosphodiesterase inhibitor. Assays are performed for 25 minutes at room temperature to achieve 5–10% hydrolysis of substrate. The negatively charged substrates are then separated from guanosine by binding to an anion-exchange resin (AG1-X8) and centrifugation or filtration, and the product is quantitated by scintillation counting in counts per minute (cpm) of the remaining soluble material. Percent inhibition is calculated as follows:

% Inhibition=100−[(cpm compound-blank)/(cpm control-blank)× 100]

Activity is expresssed as the $IC_{50}$ value, ie. the concentration required to inhibit activity of enzyme by 50 per cent.

Antihypertensive activity in rats

The ability of the compounds of the present invention to lower blood pressure can be assessed in vivo in conscious spontaneously hypertensive rats (SHR). SHR males are purchased from Taconic Farms, Germantown New York and are approximately 16–18 weeks old when anesthetized with ether. The caudal (ventral tail) artery is cannulated with polyethylene tubing (PE50) and blood pressure and heart rate are recorded as described by Baum, T. et. al, J. Cardiovasc. Pharmacol. Vol 5, pp. 655–667, (1983). Rats are placed into plastic cylindrical cages where they rapidly recover consciousness. Blood pressure and heart rate are allowed to stabilize for approximately 90 minutes prior to compound administration. Compounds are administered orally as solutions or suspensions in 0.4% aqueous methylcellulose vehicle via a feeding needle. The compound or 0.4% aqueous methylcellulose vehicle are given in a volume of 4 ml/kg to SHRs that had been fasted overnight. Activity is expressed as the fall in mean blood pressure (MBP) in millimeters of mercury (mm Hg). Compound-induced changes are compared with the changes in an appropriate placebo group.

Plasma levels:

SHRs dosed orally with test compound at 10 mpk and plasma levels were subsequently measured at intervals of 0.5, 1, 2, 3 and 4 hours. Plasma levels (µg/ml) were plotted versus hours post dosing and the area under the curve (AUC, µghr/ml) was calculated.

The following test results are compared to a previously-known compound, 2'-[[(4'-methoxy-1,1'-biphenyl) -4-yl]methyl]-5'-methyl-spiro[cyclopentane-1,7'(8'H)-[3H]imidazo-[2,1-b]purin]-4'(5'H)-one (Ref. Cpd.).

| Example Number | ACTIVITY | | | | |
|---|---|---|---|---|---|
| | PDE $IC_{50}$ | | SHR Antihypertensive | | Plasma Level |
| | Type I (nM) | Type V (nM) | Dose (po) (mpk) | Fall in MBP (mmHg) | AUC (µghr/ml) |
| 1 | 11 | 170 | 10 | −24 | 4.80 |
| 2 | 12 | 210 | 10 | −11 | 5.89 |
| 3 | 9 | 520 | 10 | −35 | 7.73 |
| Ref. Cpd. | 5 | 500 | 10 | −35 | 3.34 |

We claim:

1. A compound having the structural formula

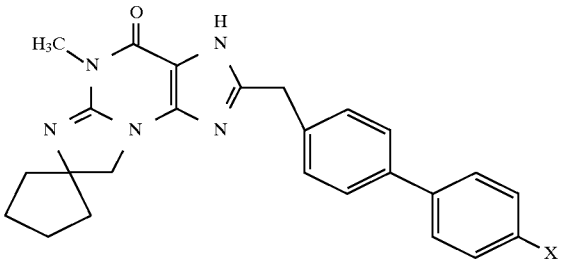

or a pharmaceutically acceptable salt thereof, wherein:
X is chloro, fluoro or bromo.

2. A pharmaceutical composition comprising an phosphodiesterase inhibitory effective amount of a compound of claim 1 in a pharmaceutically acceptable carrier.

3. A method of treating hypertension, angina, bronchoconstriction, restenosis post angioplasty, atherosclerosis, ischemia, peripheral vascular diseases, or diseases benefiting from platelet inhibition, or for increasing guanosine 3',5'-cyclic monophosphate (cGMP) levels or maintaining high cGMP levels, comprising administering an effective amount of a compound of claim 1 to a mammal in need of such treatment.

4. 2'-[[4'-Fluoro-[1,1'-biphenyl]-4-yl]methyl]-5'-methyl-spiro[cyclopentane-1,7'(8'H)-[3H]imidazo-[2,1-b]purin]-4'(5'H)-one.

5. 2'-[[4'-Chloro-[1,1'-biphenyl]-4-yl]methyl]-5'-methyl-spiro[cyclopentane-1,7'(8'H)-[3H]imidazo-[2,1-b]purin]-4'(5'H)-one.

6. 2'-[[4'-Bromo-[1,1'-biphenyl]-4-yl]methyl]-5'-methyl-spiro[cyclopentane-1,7'(8'H)-[3H]imidazo-[2,1-b]purin]-4'(5'H)-one.

* * * * *

UNITED STATES PATENT AND TRADEMARK OFFICE
CERTIFICATE OF CORRECTION

PATENT NO. : 5,824,683
DATED : OCTOBER 20, 1998
INVENTOR(S) : BRIAN A. MCKITTRICK AND DEEN TULSHIAN

It is certified that error appears in the above-identified patent and that said Letters Patent is hereby corrected as shown below:

In column 18, lines 38-39, delete "or maintaining high cGMP levels".

Signed and Sealed this

Fourth Day of May, 1999

Attest:

Q. TODD DICKINSON

*Attesting Officer*

*Acting Commissioner of Patents and Trademarks*